(12) United States Patent
Chang (10) Patent No.: US 7,947,435 B2
(45) Date of Patent: May 24, 2011

(54) NEURONAL REGENERATION MATERIAL SCREENING METHOD BY EX VIVO MODEL

(75) Inventor: Mi-Sook Chang, Seoul (KR)

(73) Assignee: Seoul National University Industry Foundation, Seoul (KR)

(*) Notice: Subject to any disclaimer, the term of this patent is extended or adjusted under 35 U.S.C. 154(b) by 617 days.

(21) Appl. No.: 11/625,189

(22) Filed: Jan. 19, 2007

(65) Prior Publication Data
US 2008/0175821 A1 Jul. 24, 2008

(51) Int. Cl.
*C12Q 1/00* (2006.01)
(52) U.S. Cl. ............................... 435/4; 435/32; 435/375
(58) Field of Classification Search .................. None
See application file for complete search history.

(56) References Cited

OTHER PUBLICATIONS

Lee Y-S et al. "aFGF Promotes Axonal Growth in Rat Spinal Cord Organotypic Slice Co-Cultures", Journal of Neurotrauma, 2002, vol. 19, No. 3, pp. 357-367.*
Crockett D.P. et al. "Number of Oligodendrocyte Progenitors Recruited to the Lesioned Spinal Cord Is Modulated by the Levels of the Cell Cycle Regulatory Protein p27Kip-1", GLIA, 2005, vol. 49, pp. 301-308, entire document (Published online, Oct. 7, 2004).*
Cho K.J. et al. "Neurons Derived From Human Mesenchymal Stem Cells Show Synaptic Transmission and Can Be Induced to Produce the Neurotransmitter Substance P By Interleukin-1alpha", Stem Cells, 2005; vol. 23, pp. 383-391.*
U2: Ho T.W. et al. TGF beta trophic factors defferentially modulate motor axon outgrowth and protection from excitotoxicity, Experimental Neurology, 2000, vol. 161, pp. 664-675.*

* cited by examiner

*Primary Examiner* — Jon P Weber
*Assistant Examiner* — Satyendra K Singh
(74) *Attorney, Agent, or Firm* — JHK Law; Joseph H. Kim (57) ABSTRACT

The present invention relates to a neuronal regeneration material screening method using ex vivo models, more precisely a neuronal regeneration material screening method using an organotypic spinal cord slice culture. The neuronal regeneration material screening method using spinal cord slices of living bodies of the present invention can be effectively applied for the development of a novel therapeutics for neurodegenerative diseases, such as spinal cord injury.

6 Claims, 6 Drawing Sheets
(5 of 6 Drawing Sheet(s) Filed in Color)

NEURONAL REGENERATION MATERIAL SCREENING METHOD BY EX VIVO MODEL

TECHNICAL FIELD

The present invention relates to a neuronal regeneration material screening method using ex vivo models, more precisely a neuronal regeneration material screening method using spinal cord slices.

BACKGROUND ART

Mesenchymal stem cells were first found in the mouse spinal cord cells, which were in the form of fibroblasts (Friedenstein et al., Cell Tissue Kinet, 20, 263-272, 1987). Mesenchymal stem cells are classified into several mesodermal series and these cells can be differentiated into various cells, that is mesenchymal stem cells are characterized by their diversity in differentiation into osteoblasts (Friedenstein et al., Cell Tissue Kinet, 20, 263-272, 1987; Abdallah et al., Bone, 39, 181-188, 2006), adipocytes (Fink et al., Stem Cells, 22, 1346-1355, 2004; Abdallah et al., Bone, 39, 181-188, 2006), endothelial cells (Kassem et al., Basic Clin Pharmacol Toxicol 95, 209-14, 2004) and neuronal cells (Woodbury et al., J Neurosci Res, 61, 364-370, 2000; Woodbury et al., J Neurosci Res, 69, 908-917, 2002; Krabbe et al., APMIS, 113, 831-844, 2005).

Through clinical trials, understanding of mesenchymal stem cells has been widened and studies on the efficiency and stability of gene therapy based on transplantation have been actively undergoing (Zhao et al., J Neurol Sci, 233, 87-91, 2005). Recently, it has been reported that bone marrow-derived mesenchymal stem cells were applied to induce regeneration of bone, myocardium and nerves (Jiang et al., Zhonghua Er Bi Yan Hou Ke Za Zhi, 37, 137-139, 2002; Kassem et al., Basic Clin Pharmacol Toxicol, 95, 209-214, 2004; Kemp et al., Leuk Lymphoma, 46, 1531-1544, 2005; Biossy et al., Cancer Res 65, 9943-9952, 2005; Krabbe et al., APMIS, 113, 831-844, 2005). In particular, this application seems to have great advantage for the treatment of various neurodegenerative diseases because the transplantation of stem cells into the wounded area not only opens the possibility of nerve replacement but also plays an important role in maintaining existing cells (Maragakis et al., Glia, 50, 145-159, 2005).

Chronic pathological phenomena occurring after short-term damage on spinal nerves have been studied and in fact characteristics or symptoms of in vivo spinal cord injury models have been reported (Krassioukov et al., J Neurotrauma, 19, 1521-1529, 2002; Lee et al., Orthop Clin North Am, 33, 311-315, 2002; Casha et al., Exp Neurol, 196, 390-400, 2005; Goldman, Nat Biotechnol, 23, 862-871, 2005). From the observation on the area neighboring damaged spinal cord was confirmed that direct damage or tissue destruction was reduced as farther from the damaged area (Buss & Schwab, Glia, 42, 424-432, 2003) and spinal cord injury was associated with the loss of neurons and glia (Goldman, Nat Biotechnol, 23, 862-871, 2005). Once the spinal cord is damaged, changes in expression of various genes and proteins are observed, which finally cause demyelination, according to recent reports (Di Giovanni et al., Proc Natl Acad Sci USA., 102, 8333-8338, 2005; Kang et al., Proteomics, 6, 2797-2812, 2006). In vivo spinal cord injury model makes the interpretation of the results from experiments difficult because of the complexity of the in vivo system. Thus, in vitro model has been preferred, since it enables the regulation from the outside of a cell and the repetition of the experiment. And it costs less. However, such in vitro model dose not have any biological activity.

Organotypic slice cultures have been used for various injury models for the study of ischemia and cytotoxicity (Krassioukov et al., J Neurotrauma, 19, 1521-1529, 2002). Spinal cord culture exhibits distinguishable dorsal horn and ventral horn and is in excellent shape as a whole, suggesting that it is easy to observe neuronal distribution (Ulich et al., J Neurophysiol., 72, 861-871, 1994; Takuma et al., Neuroscience, 109, 359-370, 2002; Hilton et al., Brain Res Brain Res Rev, 46, 191-203, 2004).

Demyelination of axon without structural damage and the disorder of saltatory conduction might be the cause of functional defect by spinal cord injury (Nicot, Brain 126, 398-412, 2003). Lysolecithin is a lipid containing detergent-like protein and has a similar activity with a membrane soluble agent exhibiting myelinated cell-specific toxicity to cause demyelination (Franklin et al., J Neurosci Res 58, 207-213, 1999; Arnett et al., Science, 306, 2111-2115, 2004). It has been known that lysolecithin causes demyelination when it is inserted in myelinated fiber in tissues such as the spinal cord and thus causes spinal cord injury in vivo. In the meantime, the loss of oligodendrocyte, a cause of various adult demyelination-associated diseases including multiple sclerosis, has been proved to be associated with demyelination of spinal cord. When the precursor cells of human oligodendrocytes were transplanted in the adult mouse brain damaged by lysolecithin, the precursor cells were rapidly differentiated into oligodendrocytes-like cells and induced remyelination of the demyelinated axon although the efficiency was lower than true myelinating cells (Goldman, Nat Biotechnol, 23, 862-871, 2005). These results suggest that axons demyelinated by lysolecithin can be remyelinated by the transplantation of mesenchymal stem cells.

The present inventors confirmed that neuronal regeneration of damaged axons in spinal cord slices could be induced after transplantation of bone marrow-derived mesenchymal stem cells into those slices which had previously been demyelinated by a toxic compound. Furthermore, the present inventors completed this invention by confirming that directional neuronal regeneration could be effectively applied as a novel treatment method for neurodegenerative diseases such as spinal cord injury.

DISCLOSURE

Technical Problem

The object of the present invention is to provide a use of directional neuronal regeneration, which is induced by transplanting mesenchymal stem cells into spinal cord slices previously demyelinated by a toxic compound, for the treatment of neurodegenerative diseases and to apply the neuronal regeneration model for the screening of a novel neuronal regeneration material.

TECHNICAL SOLUTION

To achieve the above object, the present invention provides a screening method for a neuronal regeneration material by using spinal cord slices.

The present invention also provides a method of inducing remyelination of the demyelinated axons in the spinal cord which includes the step of transplanting bone marrow-derived mesenchymal stem cells into the damaged spinal cord.

The present invention further provides a cell composition for the directional neuronal regeneration of the injured axons in the spinal cord comprising bone marrow-derived mesenchymal stem cells.

Hereinafter, the present invention is described in detail.

The present invention provides a method for screening a neuronal regeneration material comprising the following steps:

1) Culturing tissue slices obtained from the spinal cord;
2) Damaging the tissue slices in course of the culture of step 1) by treating with a toxic compound;
3) Administering neuronal regeneration material candidates to the damaged tissue slices; and
4) Selecting neuronal regeneration material candidates that exhibit significant neuronal regeneration effect, compared with the negative control untreated with such candidates.

Experimental animal models are classified as the in vivo model targeting an individual animal, the in vitro model targeting a cell culture solution and the ex vivo model targeting a live tissue. The disadvantage of in vivo model is that the regulation of various endogenous factors is difficult and thereby the result can be misinterpreted. In the meantime, the in vitro model has also disadvantages of not-guaranteeing the activity of biomaterials. The live tissue slices obtained from spinal cord of the invention can be cultured for 3 weeks since their separation is carried out promptly by using a tissue chopper. Thus, they can be used as an ex vivo system with advantages from both in vivo and in vitro systems. The system established in the present invention facilitates the study of acute and sub-acute pathophysiology in addition to enabling the regulation of associated environments with the goal of the experiment. This system has excellent reproducibility, compared with other animal models, and is economical.

As explained above, the live tissue slices of the invention can survive for 3 weeks under proper culture conditions. Thus, they can be effectively applied for screening of novel materials involved in the regeneration of damaged spinal cord. In particular, neurons of the live tissue slices can be intentionally damaged, a candidate molecule expected to induce the regeneration of the damaged neuron be administered and the slices be cultured for 2~3 weeks. Then, the regeneration level and characteristics can be observed to investigate the usability of the novel candidate material.

The optimal thickness of these spinal cord slices is 300~500 μm and more specifically 400 μm. The toxic compound of step 2) is preferably lysolecithin-induced demyelination of axons in the spinal cord. The method for confirming the regeneration effect in step 4) includes observation of the specific protein expression on neurons using immunofluorescence, observation of neuronal regeneration by histological method, and observation of apoptotic cells by TUNEL assay.

The damage in step 2) includes every neuronal damage in the spinal cord but preferably indicates demyelination. The candidate material in step 3 and in claim 1 includes compounds, growth factors, cytokines, mesenchymal stem cell-originated factors, extracellular matrix proteins, proteins involved in axonal growth, and factors involved in intracellular signal transduction.

The present invention also provides a method for inducing the directional neuronal regeneration of the injured axons in the spinal cord, including the step of transplanting bone marrow-derived mesenchymal stem cells into the damaged spinal cord slice of an animal and a cell composition for the directional neuronal regeneration of the injured spinal cord tissue.

The spinal cord was extracted from an anesthetized rat, which was cut into regular sized slices by using a tissue chopper. The spinal cord tissue slices were cultured in a proper culture medium, where lysolecithin was administered to induce demyelination (Birgbauer et al., J Neurosci Res, 78, 157-166, 2004). After inducing demyelination, the medium containing lysolecithin was replaced with a fresh medium. The bone marrow-derived mesenchymal stem cells were microinjected into dorsal column area to induce directional neuronal regeneration of injured spinal cord slice culture. Proteins specific to neurons in both injured group and test group treated with MSCs were labeled by immunofluorescent staining and observed under confocal microscope. Neuronal regeneration was also detected by histological method and apoptosis was examined by propidium idodide assay.

Figure 1:
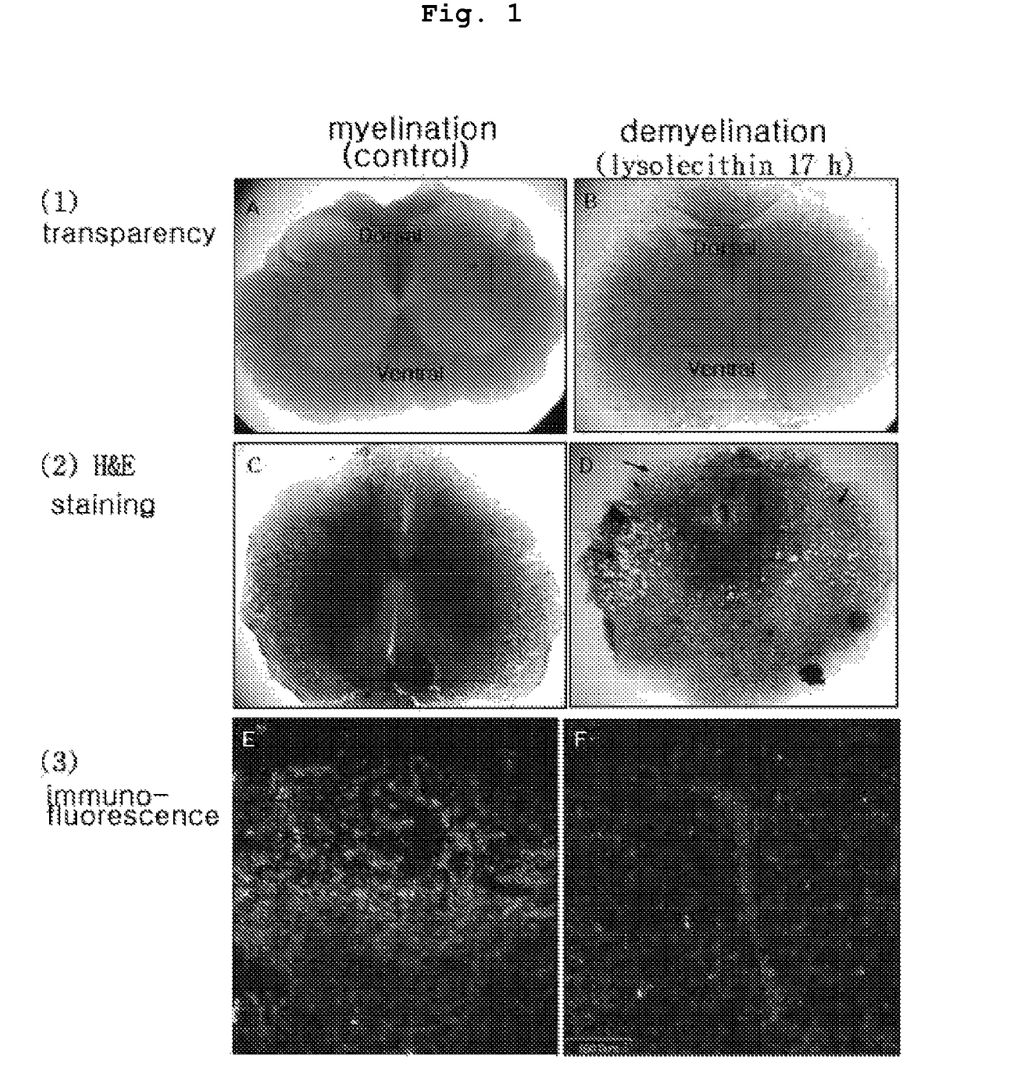
FIG. 1 is a set of photographs showing the demyelinations of spinal cord slices by lysolecithin.
Figure 2:
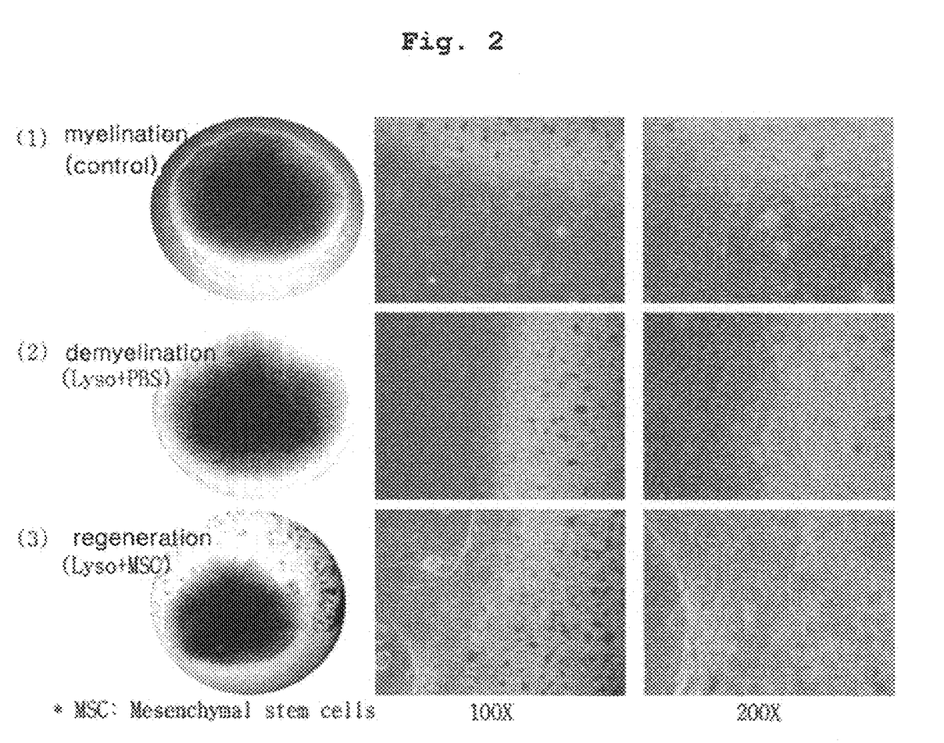
FIG. 2 is a set of photographs showing the regeneration of axons in the demyelinated spinal cord slices by the transplantation of mesenchymal stem cells.

The result confirmed that axons in the spinal cord slices were demyelinated by lysolecithin (see FIG. 1) and regenerated by transplantation of bone marrow-derived mesenchymal stem cells (see FIG. 2). During the regeneration, directional neuronal regeneration was induced from spinal cord slices to mesenchymal stem cells. Neuronal regeneration was also confirmed by detecting the increase in the expression level of proteins specific to neurons and glia by immunofluorescent method (see FIGS. 3, 4, 5 and 6).

The present invention is applicable to vertebrates, preferably mammals. The method for inducing directional neuronal regeneration of the injured spinal cord tissue by transplanting bone marrow-derived mesenchymal stem cells and a cell composition thereof can be applied to vertebrates and more preferably mammals. The method and the composition of the present invention can be effectively used as a novel treatment method for neurodegenerative diseases. Spinal cord injury is one of the neurodegenerative diseases which leads to abnormal degeneration of neurons and motor disturbance.

DESCRIPTION OF DRAWINGS

The patent or application file contains at least one drawing executed in color. Copies of this patent or patent application publication with color drawing(s) will be provided by the Office upon request and payment of the necessary fee.

The application of the preferred embodiments of the present invention is best understood with reference to the accompanying drawings, wherein.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Implantation of Mesenchymal Stem Cells

<1-1> Culture of Human Mesenchymal Stem Cells

Human mesenchymal stem cells derived from bone marrow were purchased from Cambrex Co (USA). These cells were sub-cultured twice in a mesenchymal stem cell growth medium (MSCGM). Then, they were maintained in DMEM (Invitrogen, USA) supplemented with 10% FBS (Invitrogen, USA), 100 ng/ml penicillin and 100 U/ml streptomycin (Invitrogen, USA) in a 5% $CO_2$, 37° C. incubator.

<1-2> Preparation of Spinal Cord Tissue Slices Sprague-Dawley rats at 16 days old were anesthetized and the spinal cord was extracted. The spinal cord was put into ice-cold HBSS (Hanks balanced salt solution). Thoracic and lumbar spinal cords were cult into 400 µm in thickness by using a tissue chopper (McIlwain tissue chopper, The Mickle Laboratory Engineering Co. LTD, England). Several spinal cord slices were loaded on 0.4 µm filter (Millicell-CM filters, Millipore, USA) placed on a 6 well plate. The spinal cord slices were cultured in 1 ml of 25% horse serum (Invitrogen, USA) containing 50% MEM (Invitrogen, USA) supplemented with Earl's salts, 25% HBSS (Invitrogen, USA), 20 mM HEPES (Sigma, USA) and 6 mg/ml of D-glucose (Duchefa, Netherlands). The culture conditions were 5% $CO_2$, 37° C. and the medium was replaced with a fresh medium twice a week.

<1-3> Demyelination by Lysolecithin

The spinal cord slices were cultured in vitro (DIV, days in vitro) for 7 days. After treating 0.5 mg/ml of lysolecithin, the slices were cultured at 37° C. for 17 hours to induce demyelination of axons (Birgbauer et al., J Neurosci Res, 78, 157-166, 2004). After inducing demyelination, the medium containing lysolecithin was replaced with 1 ml of fresh medium.

<1-4> Cell Transplantation

Mesenchymal stem cells of Example <1-1> were transplanted in dorsal column of the slices prepared in Example <1-2> by using an Eppendorf Cell Tram Injector (Eppendorf, Germany).

Example 2

Confirmation of Neuronal Regeneration

<2-1> Immunofluorescent Staining

Spinal cord slices were fixed in 4% formaldehyde overnight at 4° C. and then permeated with 0.5% Triton X-100 for 10 minutes, followed by blocking with 3% BSA containing 0.1% Triton X100 for one hour. Then, the slices were treated with primary antibodies such as anti-MBP rabbit antibody (myelin basic protein; Chemicon, USA), anti-NF-M rabbit antibody (Neurofilament M; Chemicon, USA), anti-Hu mouse antibody (Human Nuclei; Chemicon, USA), PI (propidium iodide, Sigma, USA) or anti-CNPase mouse antibody (cyclin nucleotide phosphodiesterase; Covance, USA) and then further cultured overnight at 4° C. Then, they were incubated with the secondary antibodies such as anti-mouse goat Alexa488 (green, molecular probe, USA) or anti-rabbit Cy3 (red, Jackson Lab, USA).

Figure 3:
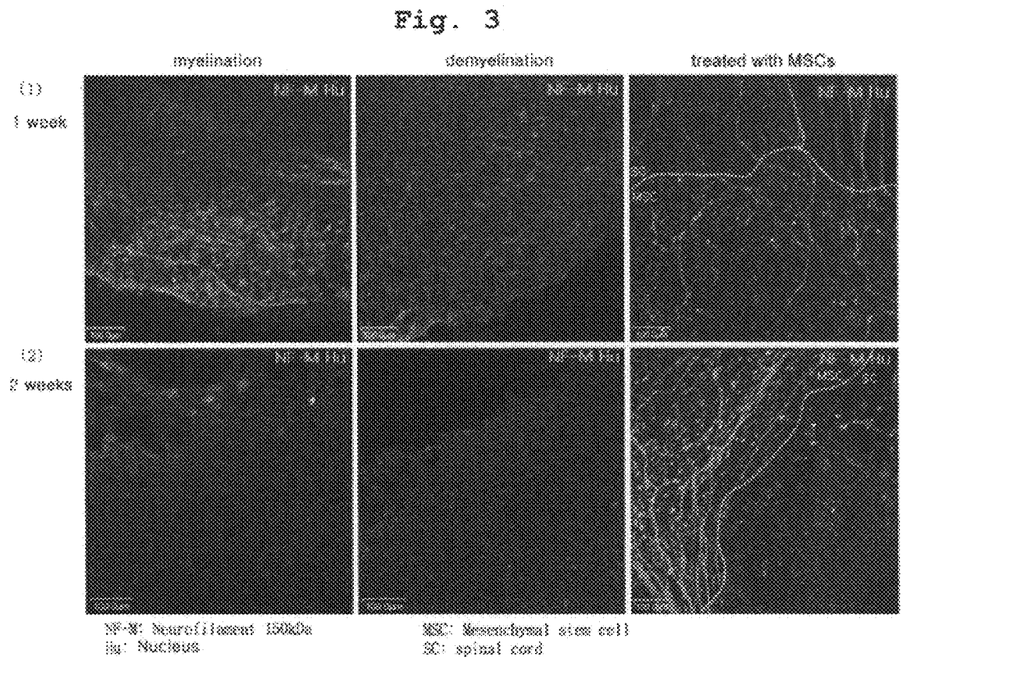
FIG. 3 is a set of photographs showing the result of immunofluorescence of neurofilament of the axons in the spinal cord (150 kDa), performed to detect regeneration of the demyelinated axons in spinal cord slices by the transplantation of mesenchymal stem cells.
Figure 4:
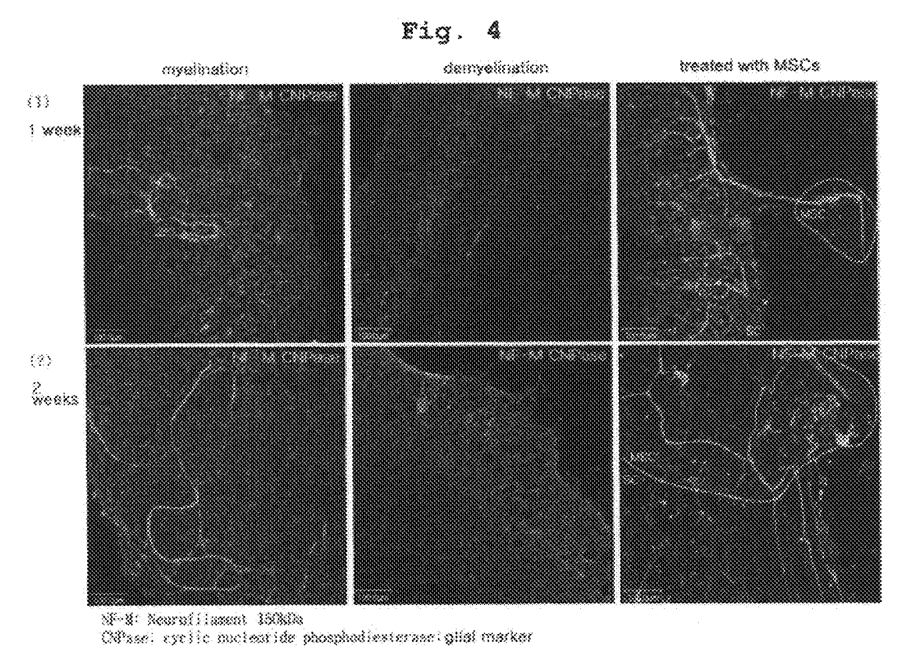
FIG. 4 is a set of photographs showing the result of immunofluorescence of neurofilament (150 kDa), performed to detect regeneration of the demyelinated axons in spinal cord slices by the transplantation of mesenchymal stem cells.
Figure 5:
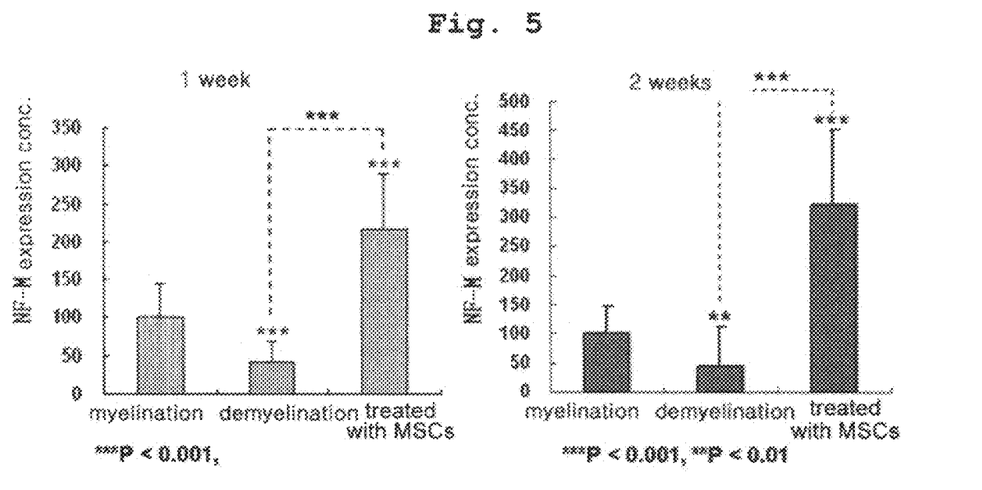
FIG. 5 is a set of graphs showing the increase of the expression of neurofilament (150 kDa) by regeneration of the demyelinated axons in spinal cord slices by the transplantation of mesenchymal stem cells.
Figure 6:
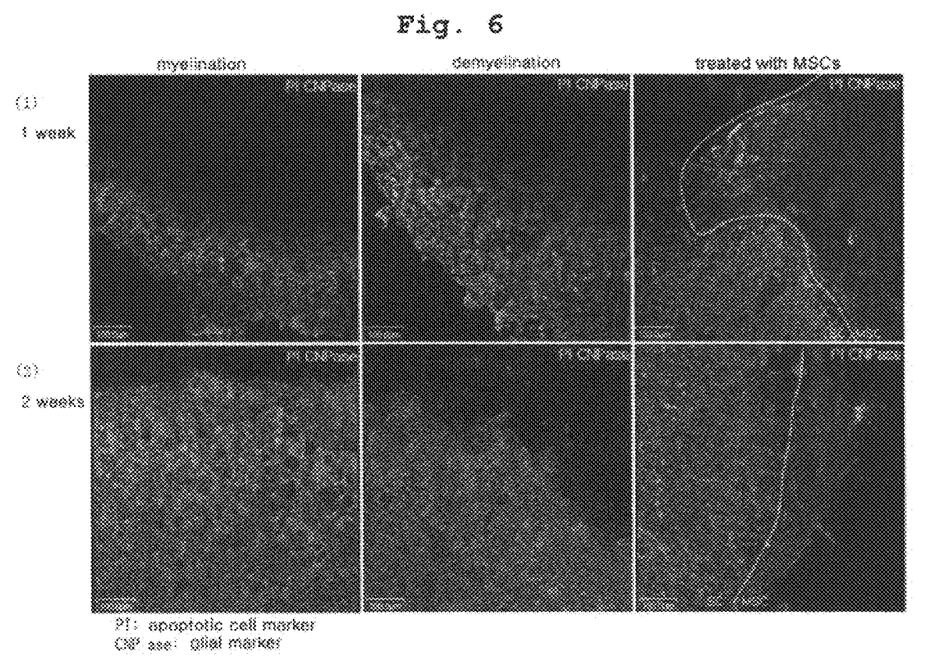
FIG. 6 is a set of photographs showing the result of immunofluorescence of P1 and CNPase, performed to detect regeneration of the demyelinated axons in spinal cord slices by the transplantation of mesenchymal stem cells.

In result, MBP expression was decreased in spinal cord slices treated with lysolecithin, compared with the control (FIG. 1). The immunofluorescence assay which was performed to examine the expression of NF-M also confirmed that directional regeneration was induced from spinal cord slices to mesenchymal stem cells (FIGS. 3 and 4). In addition, the expression of glial marker (CNPase) was increased (FIGS. 4 and 6), while apoptotic cell marker (PI) was decreased in the group transplanted with mesenchymal stem cells. These results suggest the neuroregeneration effect of mesenchymal stem cells (FIG. 6).

<2-2> Histological Analysis

Spinal cord tissue slices were fixed in 10% formalin for one hour. To detect myelin expression, the tissue slices were stained with 0.1% Luxol fast blue. To distinguish neurons from the other cells in tissue, the slices were counter-stained with H&E.

In result, serious demyelination was observed in spinal cord slices treated with lysolecithin, compared with the control (FIG. 1. Regeneration was also observed by the transplantation of mesenchymal stem cells (FIG. 2).

INDUSTRIAL APPLICABILITY

As explained hereinbefore, the method for inducing neuronal regeneration in the demyelinated area by transplanting bone marrow-derived mesenchymal stem cells and the method for screening a neuronal regeneration material using ex vivo models of spinal cord live tissue slices of the present invention can be effectively applied as a novel treatment method for neurodegenerative diseases.

Those skilled in the art will be appreciated that the conception and specific embodiments disclosed in the foregoing description may be readily utilized as a basis for modifying or designing other embodiments for carrying out the same purposes of the present invention. Those skilled in the art will be also appreciated that such equivalent embodiments do not depart from the spirit and scope of the invention as set forth in the appended claims.

The invention claimed is:

1. A method for screening for a neuronal regeneration material comprising the following steps:
   1) culturing, on a filter, a single tissue slice obtained from the lumbar spinal cord of a mammal in a well, wherein the thickness of the tissue slice is 400 µm;
   2) damaging the tissue slice in the course of culturing the single tissue slice of step 1) by treating with a toxic compound, which induces demyelination of axons in the spinal cord;
   3) contacting neuronal regeneration material candidates to the damaged tissue slice; and
   4) selecting a neuronal regeneration material candidate that induces significant directional neuronal regeneration, from the tissue slice to the neuronal regeneration material candidate, compared with the negative control untreated with the neuronal regeneration material candidates; wherein a spinal cord slice treated with mesenchymal stem cells is used as a positive control and the negative control group is a spinal cord slice untreated with the mesenchymal stem cells.

2. The method according to claim 1, wherein the neuronal regeneration material candidate includes a compound, a growth factor, a cytokine, a mesenchymal stem cell-originated factor, an extracellular matrix protein, a protein involved in the axonal growth and a factor involved in intracellular signal transduction.

3. The method according to claim 1, wherein the spinal cord tissue slice is live tissue cut by a tissue chopper.

4. The method according to claim 1, wherein the toxic compound of step 2 is lysolecithin.

5. The method according to claim 1, wherein the mammal is a rat.

6. The method according to claim 5, wherein the spinal cord is isolated from a rat at 16 days old.

* * * * *